US012543784B2

(12) United States Patent
Aller et al.

(10) Patent No.: US 12,543,784 B2
(45) Date of Patent: Feb. 10, 2026

(54) AEROSOL DELIVERY DEVICE

(71) Applicant: RAI Strategic Holdings, Inc., Winston-Salem, NC (US)

(72) Inventors: Jared Aller, Winston-Salem, NC (US); William D. Webb, San Francisco, CA (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 1149 days.

(21) Appl. No.: 17/211,424

(22) Filed: Mar. 24, 2021

(65) Prior Publication Data

US 2022/0304378 A1 Sep. 29, 2022

(51) Int. Cl.
*A24F 40/42* (2020.01)
*A24F 40/46* (2020.01)
(Continued)

(52) U.S. Cl.
CPC .............. *A24F 40/42* (2020.01); *A24F 40/46* (2020.01); *A24F 40/50* (2020.01); *A24F 42/60* (2020.01);
(Continued)

(58) Field of Classification Search
CPC .......... A24F 40/42; A24F 40/46; A24F 40/50; A24F 42/60; A24F 40/40; A24F 40/10; A24F 7/00; A24F 40/95; A24F 40/485; A24F 40/20; A24F 40/53; A24F 40/70; A61M 15/0021; A61M 15/0086; A61M 15/06; A61M 2205/02; A61M 2205/583; A61M 2205/8262; A61M 15/00; A61M 11/042; A61M 2205/8206; A61M 11/041; B65D 25/38
USPC ........................ 131/329, 273, 328, 194, 347; 128/202.21, 200.14, 203.12, 203.27, 128/204.17, 200.23, 203.17
See application file for complete search history.

(56) References Cited

U.S. PATENT DOCUMENTS

| | | | |
|---|---|---|---|
| 2,057,353 | A | 10/1936 | Whittemore, Jr. |
| 2,104,266 | A | 1/1938 | McCormick |

(Continued)

FOREIGN PATENT DOCUMENTS

| | | |
|---|---|---|
| CN | 1541577 | 11/2004 |
| CN | 2719043 | 8/2005 |

(Continued)

*Primary Examiner* — Brandy S Lee
*Assistant Examiner* — Tina Zhang
(74) *Attorney, Agent, or Firm* — Womble Bond Dickinson (US) LLP

(57) ABSTRACT

A cartridge for use in an aerosol delivery device, the cartridge including: an outer housing configured to contain at least an aerosolizable composition, the outer housing including an exit portal at a proximal end thereof for passage of an aerosol; and a bottom cap positioned at a distal end of the outer housing that is configured for insertion into a receiving chamber of a control device of the aerosol delivery device. The outer housing defines a front face portion and a rear face portion interconnected with sidewalls, wherein the front face portion has an asymmetrical configuration relative to the rear face portion, such asymmetrical configuration being effective such that the cartridge engages the control device of the aerosol delivery device in only a single orientation. A control device is also provided herein.

18 Claims, 9 Drawing Sheets

(51) Int. Cl.

| | |
|---|---|
| ***A24F 40/50*** | (2020.01) |
| ***A24F 42/60*** | (2020.01) |
| ***A61M 15/00*** | (2006.01) |
| ***A61M 15/06*** | (2006.01) |

(52) U.S. Cl.
CPC .... *A61M 15/0021* (2014.02); *A61M 15/0086* (2013.01); *A61M 15/06* (2013.01); *A61M 2205/02* (2013.01); *A61M 2205/583* (2013.01); *A61M 2205/8262* (2013.01)

(56) References Cited

U.S. PATENT DOCUMENTS

| | | | | |
|---|---|---|---|---|
| 3,200,819 | A | 8/1965 | Gilbert | |
| 4,922,901 | A | 5/1990 | Brooks et al. | |
| 5,060,671 | A | 10/1991 | Counts et al. | |
| 5,093,894 | A | 3/1992 | Deevi et al. | |
| 5,894,841 | A | 4/1999 | Voges | |
| 6,125,853 | A | 10/2000 | Susa et al. | |
| 6,155,268 | A | 12/2000 | Takeuchi | |
| 7,117,867 | B2 | 10/2006 | Cox et al. | |
| 7,832,410 | B2 | 11/2010 | Hon | |
| 8,314,591 | B2 | 11/2012 | Terry et al. | |
| 8,365,742 | B2 | 2/2013 | Hon | |
| 8,499,766 | B1 | 8/2013 | Newton | |
| 8,528,569 | B1 | 9/2013 | Newton | |
| 8,833,364 | B2 | 9/2014 | Buchberger | |
| 9,220,304 | B2 | 12/2015 | Greim | |
| 9,462,831 | B2 | 10/2016 | Liu | |
| 9,877,508 | B2 | 1/2018 | Kane | |
| 9,999,258 | B2 | 6/2018 | Newcomb et al. | |
| 10,015,990 | B2 | 7/2018 | Mironov | |
| 10,028,537 | B1 | 7/2018 | Hawes et al. | |
| 10,058,125 | B2 | 8/2018 | Worm et al. | |
| 10,058,129 | B2 | 8/2018 | Monsees et al. | |
| 10,064,432 | B2 | 9/2018 | Hawes et al. | |
| 10,070,669 | B2 | 9/2018 | Monsees et al. | |
| 10,080,851 | B2 | 9/2018 | Davidson et al. | |
| 10,085,481 | B2 | 10/2018 | Verleur et al. | |
| 10,092,037 | B2 | 10/2018 | Tucker et al. | |
| 10,104,913 | B2 | 10/2018 | Lau et al. | |
| 10,117,463 | B2 | 11/2018 | Thomas | |
| 10,117,465 | B2 | 11/2018 | Monsees et al. | |
| 10,117,466 | B2 | 11/2018 | Monsees et al. | |
| 10,117,467 | B2 | 11/2018 | Hawes et al. | |
| 10,201,190 | B2 | 2/2019 | Monsees et al. | |
| D874,720 | S | 2/2020 | Hawes et al. | |
| 10,709,173 | B2 | 7/2020 | Monsees et al. | |
| 2005/0016550 | A1 | 1/2005 | Katase | |
| 2006/0196518 | A1 | 9/2006 | Hon | |
| 2008/0092912 | A1 | 4/2008 | Robinson et al. | |
| 2009/0095311 | A1 | 4/2009 | Hon | |
| 2009/0126745 | A1 | 5/2009 | Hon | |
| 2009/0151717 | A1 | 6/2009 | Bowen et al. | |
| 2009/0188490 | A1 | 7/2009 | Hon | |
| 2009/0272379 | A1 | 11/2009 | Thorens et al. | |
| 2009/0320863 | A1 | 12/2009 | Fernando et al. | |
| 2010/0197565 | A1* | 8/2010 | Smutney ................ | A61K 38/28 514/1.1 |
| 2011/0094523 | A1 | 4/2011 | Thorens et al. | |
| 2011/0126848 | A1 | 6/2011 | Zuber et al. | |
| 2011/0155718 | A1 | 6/2011 | Greim et al. | |
| 2011/0168194 | A1 | 7/2011 | Hon | |
| 2011/0265806 | A1 | 11/2011 | Alarcon et al. | |
| 2013/0037041 | A1 | 2/2013 | Worm et al. | |
| 2013/0042865 | A1 | 2/2013 | Monsees et al. | |
| 2013/0087160 | A1 | 4/2013 | Gherghe | |
| 2013/0168880 | A1 | 7/2013 | Duke | |
| 2013/0306084 | A1 | 11/2013 | Flick | |
| 2013/0319435 | A1 | 12/2013 | Flick | |
| 2014/0000638 | A1 | 1/2014 | Sebastian et al. | |
| 2014/0096781 | A1 | 4/2014 | Sears et al. | |
| 2014/0096782 | A1 | 4/2014 | Ampolini et al. | |
| 2014/0253144 | A1 | 9/2014 | Novak et al. | |
| 2014/0261408 | A1 | 9/2014 | DePiano et al. | |
| 2014/0261486 | A1 | 9/2014 | Potter et al. | |
| 2014/0261487 | A1 | 9/2014 | Chapman et al. | |
| 2014/0366898 | A1 | 12/2014 | Monsees et al. | |
| 2015/0020832 | A1 | 1/2015 | Greim et al. | |
| 2015/0150308 | A1 | 6/2015 | Monsees et al. | |
| 2015/0164142 | A1 | 6/2015 | Li et al. | |
| 2015/0208729 | A1 | 7/2015 | Monsees et al. | |
| 2015/0313287 | A1 | 11/2015 | Verleur et al. | |
| 2016/0345629 | A1 | 12/2016 | Mironov | |
| 2017/0027226 | A1 | 2/2017 | Mironov et al. | |
| 2017/0071256 | A1 | 3/2017 | Verleur et al. | |
| 2017/0095005 | A1 | 4/2017 | Monsees et al. | |
| 2017/0135404 | A1 | 5/2017 | Reevell | |
| 2017/0135405 | A1 | 5/2017 | Reevell | |
| 2017/0143042 | A1 | 5/2017 | Batista et al. | |
| 2017/0215485 | A1 | 8/2017 | Zitzke | |
| 2017/0231281 | A1 | 8/2017 | Hatton et al. | |
| 2017/0231282 | A1 | 8/2017 | Hatton et al. | |
| 2017/0325289 | A1 | 11/2017 | Liu | |
| 2017/0340011 | A1 | 11/2017 | Batista | |
| 2017/0340012 | A1 | 11/2017 | Mironov et al. | |
| 2017/0347711 | A1 | 12/2017 | Litten et al. | |
| 2017/0347712 | A1 | 12/2017 | Singh | |
| 2018/0000157 | A1 | 1/2018 | Batista et al. | |
| 2018/0000160 | A1 | 1/2018 | Taschner et al. | |
| 2018/0014575 | A1 | 1/2018 | Fursa | |
| 2018/0020731 | A1 | 1/2018 | Rasmussen et al. | |
| 2018/0020736 | A1 | 1/2018 | Silvestrini | |
| 2018/0035717 | A1 | 2/2018 | Batista | |
| 2018/0042306 | A1 | 2/2018 | Atkins et al. | |
| 2018/0043114 | A1 | 2/2018 | Bowen et al. | |
| 2018/0070645 | A1 | 3/2018 | Monsees et al. | |
| 2018/0077967 | A1 | 3/2018 | Hatton et al. | |
| 2018/0084828 | A1 | 3/2018 | Phillips et al. | |
| 2018/0084831 | A1 | 3/2018 | Mironov | |
| 2018/0103685 | A1 | 4/2018 | Yener | |
| 2018/0132525 | A1 | 5/2018 | Patil et al. | |
| 2018/0140019 | A1 | 5/2018 | Guo et al. | |
| 2018/0177230 | A1 | 6/2018 | Hawes et al. | |
| 2018/0213850 | A1 | 8/2018 | Brinkley et al. | |
| 2018/0242643 | A1 | 8/2018 | Silvestrini et al. | |
| 2018/0280637 | A1 | 10/2018 | Mayle et al. | |
| 2018/0295888 | A1 | 10/2018 | Newcomb et al. | |
| 2018/0296777 | A1 | 10/2018 | Terry et al. | |
| 2019/0124996 | A1* | 5/2019 | Qiu ......................... | A24F 40/40 |
| 2019/0261689 | A1* | 8/2019 | Bowen .................. | A61M 15/06 |
| 2019/0350262 | A1* | 11/2019 | Saygili ...................... | A24F 7/00 |
| 2020/0029619 | A1* | 1/2020 | Sundberg .................. | A24F 7/02 |
| 2020/0288788 | A1 | 9/2020 | Vora et al. | |
| 2020/0376210 | A1* | 12/2020 | Simpson ................. | A24F 40/10 |

FOREIGN PATENT DOCUMENTS

| | | |
|---|---|---|
| CN | 201379072 | 1/2010 |
| EP | 1 618 803 | 1/2006 |
| WO | WO 2004/080216 | 9/2004 |
| WO | WO 2005/099494 | 10/2005 |
| WO | WO 2007/131449 | 11/2007 |
| WO | WO 2016/026811 | 2/2016 |
| WO | WO 2017/051006 | 9/2016 |
| WO | WO 2017/207442 | 5/2017 |
| WO | WO 2018/167166 | 9/2018 |
| WO | WO 2018/202732 | 11/2018 |
| WO | WO 2019/185745 | 10/2019 |
| WO | 2020210821 A1 | 10/2020 |

* cited by examiner

AEROSOL DELIVERY DEVICE

TECHNOLOGY FIELD

The present disclosure relates to aerosol provision systems such as smoking articles designed to deliver at least one substance to a user.

BACKGROUND

Many aerosol provision systems and in particular non-combustible aerosol provision systems have been proposed through the years as improvements upon, or alternatives to, smoking products that require combusting tobacco for use. These systems are generally designed to deliver at least one substance to a user, such as to satisfy a particular "consumer moment." To this end, the substance may include constituents that impart a physiological effect on the user, a sensorial effect on the user, or both. The substance may be generally present in an aerosol-generating material that may contain one or more constituents of a range of constituents, such as active substances, flavors, aerosol-former materials and other functional materials like fillers.

Aerosol provision systems include, for example, vapor products commonly known as "electronic cigarettes," "e-cigarettes" or electronic nicotine delivery systems (ENDS), as well as heat-not-burn products including tobacco heating products (THPs) and carbon-tipped tobacco heating products (CTHPs). Many of these products take the form of a system including a device and a consumable, and it is the consumable that includes the material from which the substance to be delivered originates. Typically, the device is reusable, and the consumable is single-use (although some consumables are refillable). Therefore, in many cases, the consumable is sold separately from the device, and often in a multipack. Moreover, subsystems and some individual components of devices or consumables may be sourced from specialist manufacturers.

BRIEF SUMMARY

Example implementations of the present disclosure are directed to an aerosol delivery device, wherein the device is configured such that the cartridge is only insertable into the control body of the device in one orientation and a viewing window is only visible from one side of the device.

The present disclosure relates to aerosol delivery devices, methods of forming such devices, and elements of such devices. The disclosure particularly relates to an aerosol delivery device and a cartridge for use in an aerosol delivery device. In this regard, various embodiments of the disclosure provide an aerosol delivery device and/or a cartridge with advantageous usability features. The present disclosure includes, without limitation, the following example implementations.

Some example implementations provide a cartridge for use in an aerosol delivery device, the cartridge comprising: an outer housing configured to contain at least an aerosolizable composition, the outer housing including an exit portal at a proximal end thereof for passage of an aerosol; a bottom cap defining a distal end of the outer housing that is configured for insertion into a receiving chamber of a control device; wherein the outer housing defines a front face portion and a rear face portion interconnected with sidewalls such that the outer housing has a width defined between the sidewalls and a thickness defined between the front face portion and the rear face portion, the width being greater than the thickness; and wherein the front face portion and the rear face portion are substantially asymmetrical such that the cartridge engages a control device in only a single orientation.

It is noted that the aerosol precursor composition can be present in a variety of forms, such as being in the form of a liquid or gel at ambient conditions. If desired, the aerosol precursor composition alternatively can be in the form of a solid at ambient conditions. In specific embodiments, at least a portion of the aerosol precursor composition can be in the form of a gel that is coated on the heater element, for example. In some embodiments, the aerosol precursor composition can be coated on, adsorbed by, or absorbed in a carrier material. Further, the carrier material can be positioned within the article (e.g., within the tank).

In some example implementations of the cartridge of any preceding example implementation, or any combination of any preceding example implementations, a mouthpiece is situated at the proximal end of the outer housing, and wherein the exit portal is defined through the mouthpiece.

In some example implementations of the cartridge of any preceding example implementation, or any combination of any preceding example implementations, the mouthpiece has a window defined in a front side of the mouthpiece.

In some example implementations of the cartridge of any preceding example implementation, or any combination of any preceding example implementations, the mouthpiece is configured to engage a proximal end of the tank.

In some example implementations of the cartridge of any preceding example implementation, or any combination of any preceding example implementations, the bottom cap is configured to engage a distal end of the outer housing.

In some example implementations of the cartridge of any preceding example implementation, or any combination of any preceding example implementations, the heating assembly defines a vaporization chamber and is configured to heat the aerosolizable composition to generate an aerosol.

In some example implementations of the cartridge of any preceding example implementation, or any combination of any preceding example implementations, the heating assembly comprises a flat heating member and a liquid transport element, and wherein the flat heating member and the liquid transport element are installed in a curved orientation.

In some example implementations of the cartridge of any preceding example implementation, or any combination of any preceding example implementations, the cartridge further comprises a vaporization chamber defined by the bottom cap and the heating assembly.

In some example implementations of the cartridge of any preceding example implementation, or any combination of any preceding example implementations, the tank further defines a reservoir cavity configured to hold the aerosolizable composition.

In some example implementations of the cartridge of any preceding example implementation, or any combination of any preceding example implementations, an aerosol path is defined through the outer housing and the exit portal.

In some example implementations of the cartridge of any preceding example implementation, or any combination of any preceding example implementations, the tank comprises a tank front face portion and a tank rear face portion interconnected with tank sidewalls, and wherein only the tank front face portion or a portion thereof is visible when the cartridge is engaged with the control device.

In some example implementations of the cartridge of any preceding example implementation, or any combination of any preceding example implementations, the front face portion of the outer housing comprises a viewing window, and wherein at least a portion of the tank is visible through the viewing window.

In some example implementations of the cartridge of any preceding example implementation, or any combination of any preceding example implementations, the cartridge comprises a viewing window through which at least a portion of the tank is visible, and wherein an outer housing of the control device does not define any portion of the viewing window.

In some example implementations of the cartridge of any preceding example implementation, or any combination of any preceding example implementations, at least a portion of a surface of the tank is transparent.

Some example implementations provide a control device of an aerosol delivery device, the control unit comprising: an outer housing formed of a wall extending from a distal end to a proximal end and defining a front face and a rear face interconnected with sidewalls, the rear face of the wall extending a greater distance than the front face of the wall so as to define a receiving chamber at the proximal end that is configured to receive a cartridge in only a single orientation; a power source positioned within the outer housing; and a control component positioned within the outer housing.

In some example implementations of the control device of any preceding example implementation, or any combination of any preceding example implementations, the control device further comprises a sleeve configured to substantially cover the outer housing of the control device.

In some example implementations of the control device of any preceding example implementation, or any combination of any preceding example implementations, the cartridge comprises a tank configured to contain an aerosolizable composition and a viewing window through which at least a portion of the tank is visible, and wherein the outer housing of the control device does not define any portion of the viewing window.

In some example implementations of the control device of any preceding example implementation, or any combination of any preceding example implementations, at least a portion of a surface of the tank is transparent.

In some example implementations of the control device of any preceding example implementation, or any combination of any preceding example implementations, the receiving chamber comprises at least one electrical connector positioned therein, wherein the at least one electrical connector is configured to electrically connect the control device to the cartridge.

In some example implementations of the control device of any preceding example implementation, or any combination of any preceding example implementations, the control component is configured at least in part to control the amount of electric power provided to the heating member of the cartridge.

In some example implementations of the control device of any preceding example implementation, or any combination of any preceding example implementations, the outer housing is formed from a metal, a plastic, a ceramic, a glass, or a combination thereof.

In some example implementations of the control device of any preceding example implementation, or any combination of any preceding example implementations, the control device is configured to be interchangeably connectable with a first cartridge to form a first functioning vaporization system having a first set of characteristics, and a second cartridge to form a second functioning vaporization system having a second, different set of characteristics.

In some example implementations of the control device of any preceding example implementation, or any combination of any preceding example implementations, the control device further comprises an external connector configured for electrical contact with the control device.

In some example implementations of the control device of any preceding example implementation, or any combination of any preceding example implementations, the external connector is configured for connecting the control device to one or more of an external connector, a docking station, a power source, or a data source.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURES

Figure 1B:
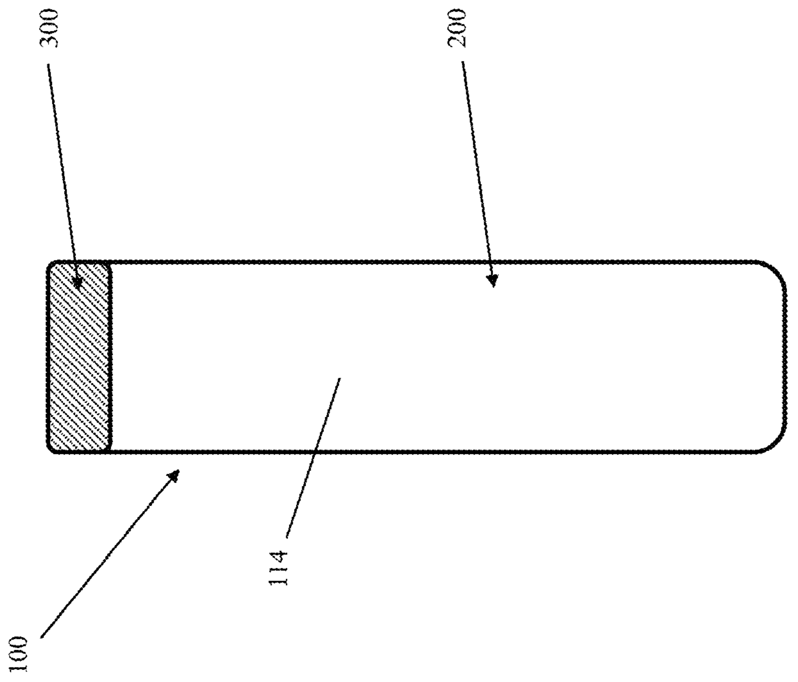
Figure 1A:
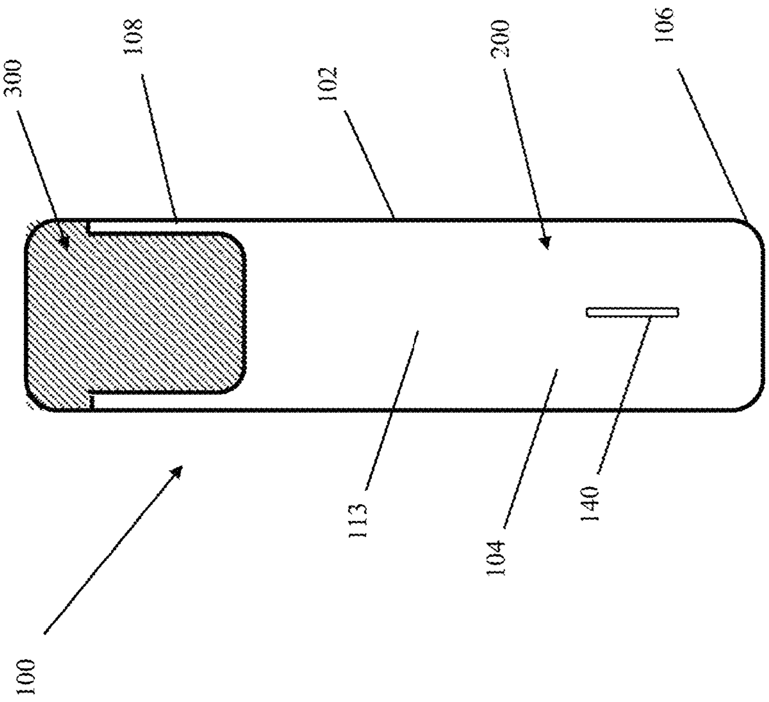
Figure 3:
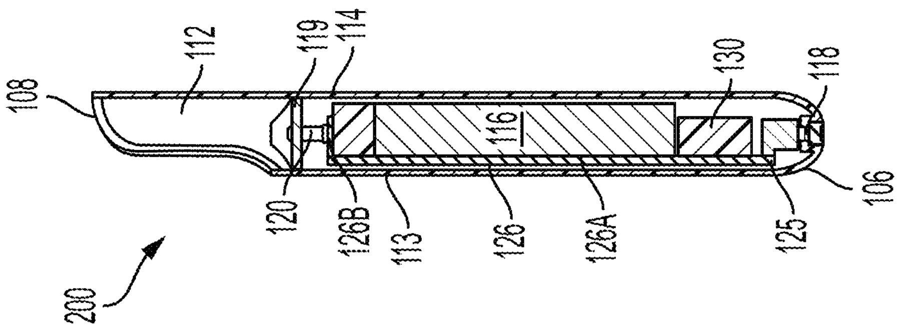
Figure 2:
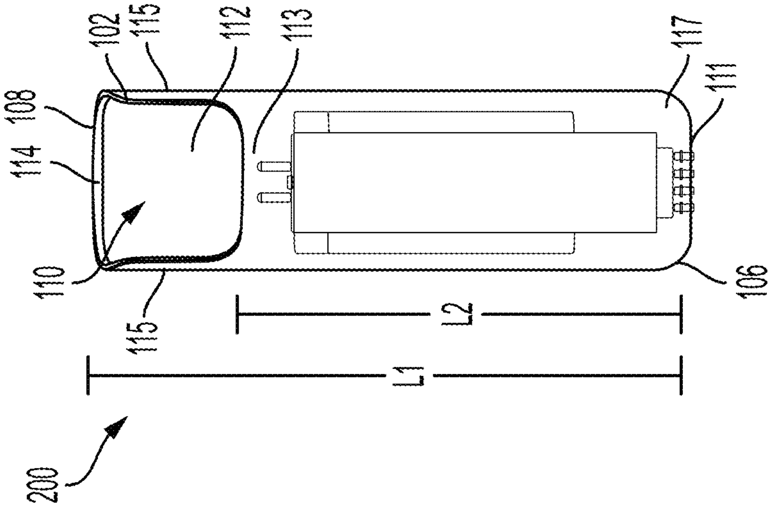
Figure 4:
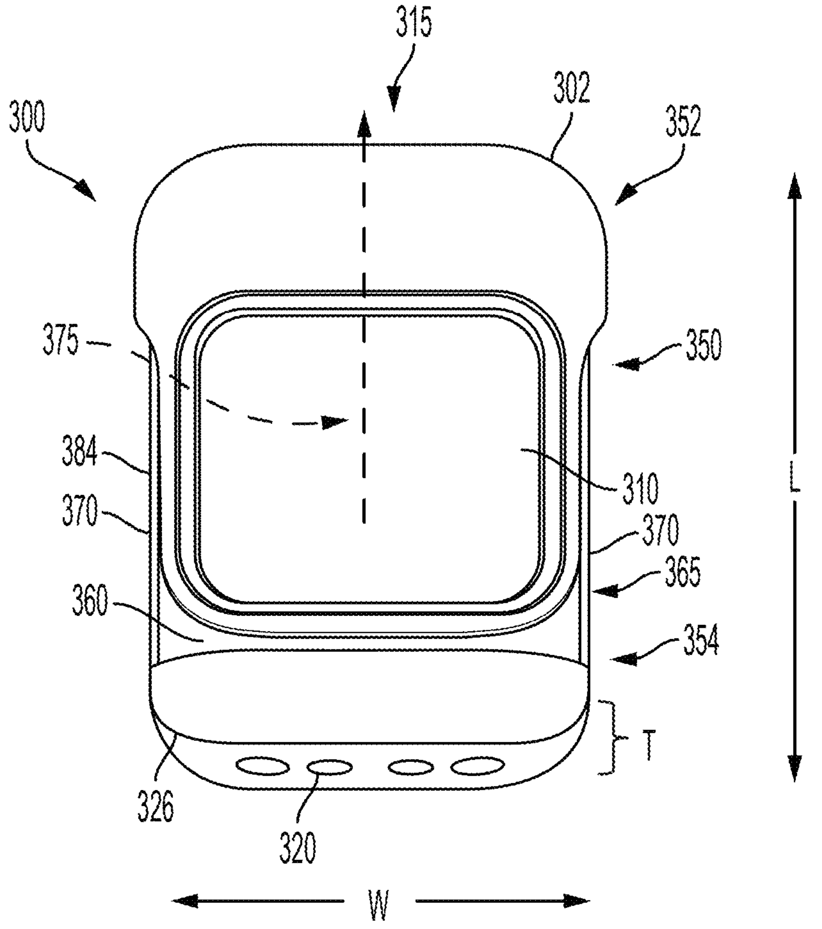
Figure 5B:
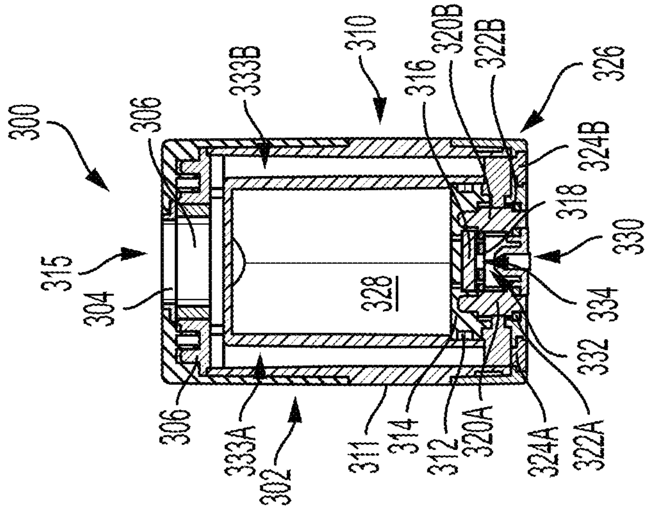
Figure 5A:
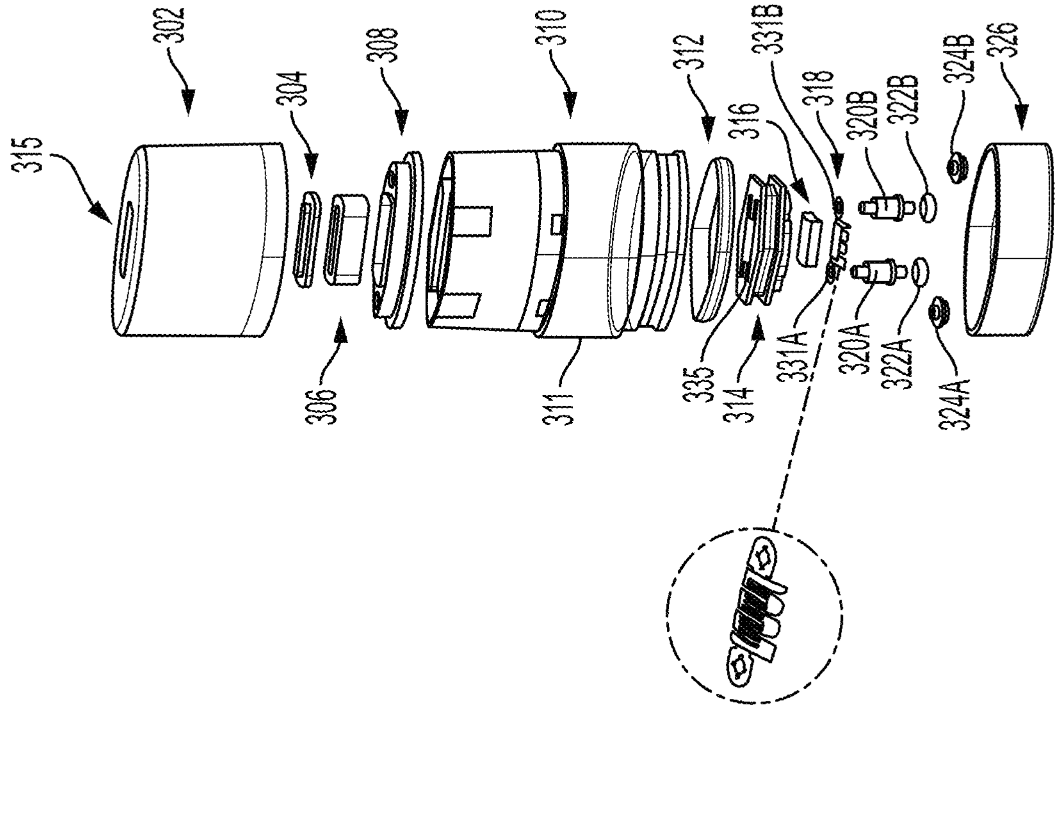
Figure 6B:
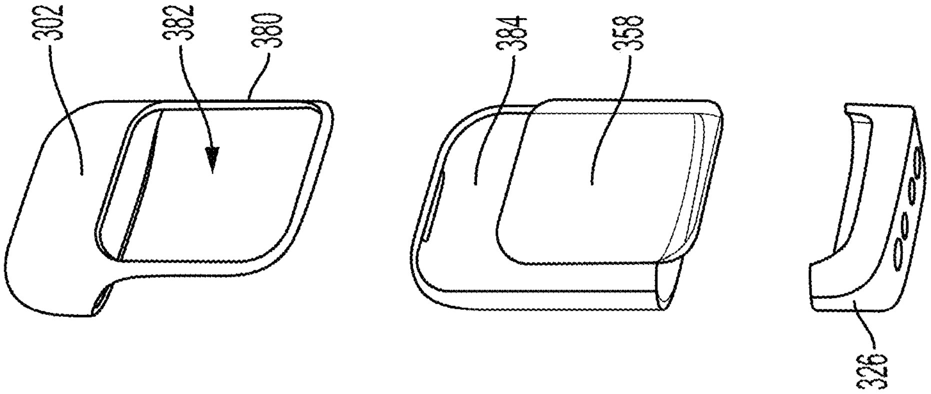
Figure 6A:
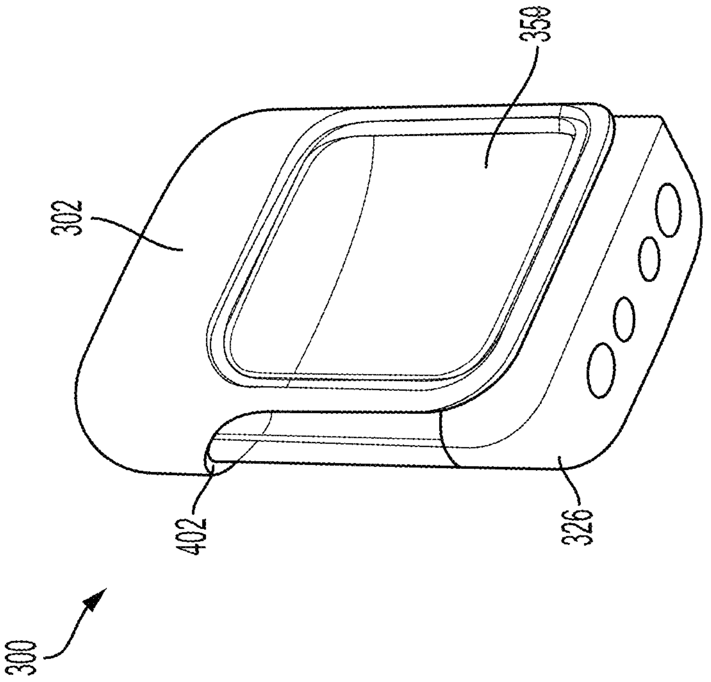
Figure 7B:
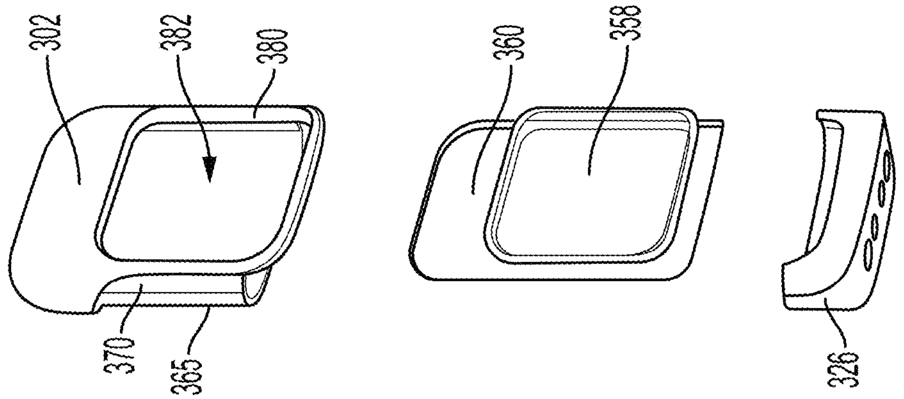
Figure 7A:
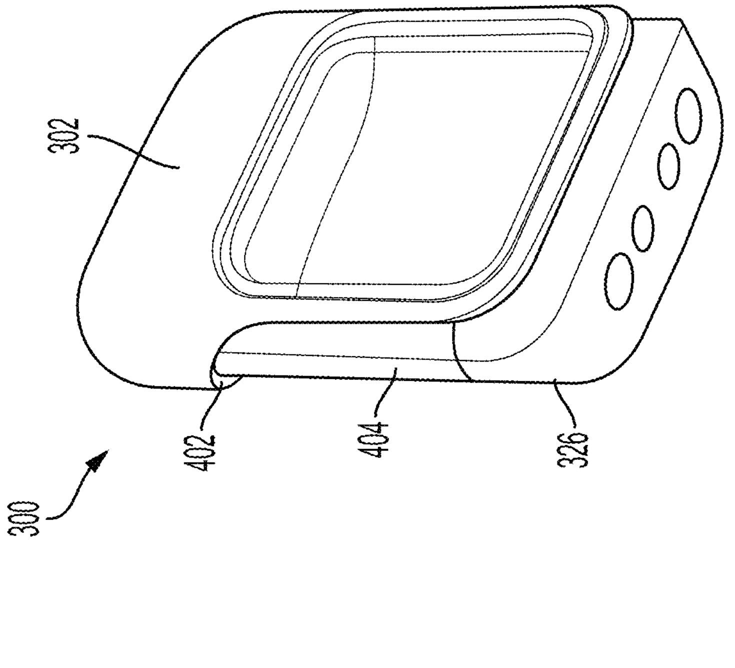
Figure 8B:
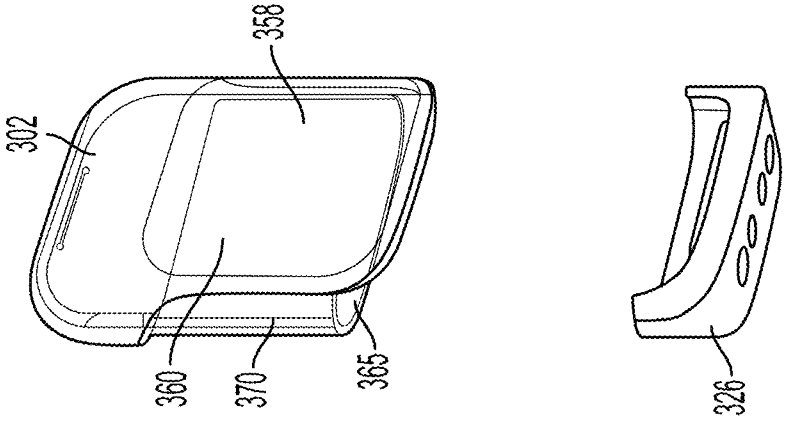
Figure 8A:
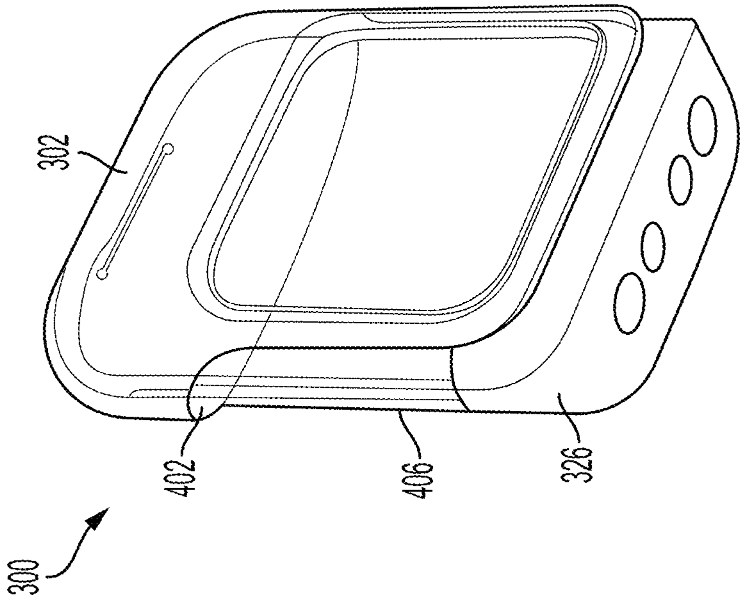
Figure 9:
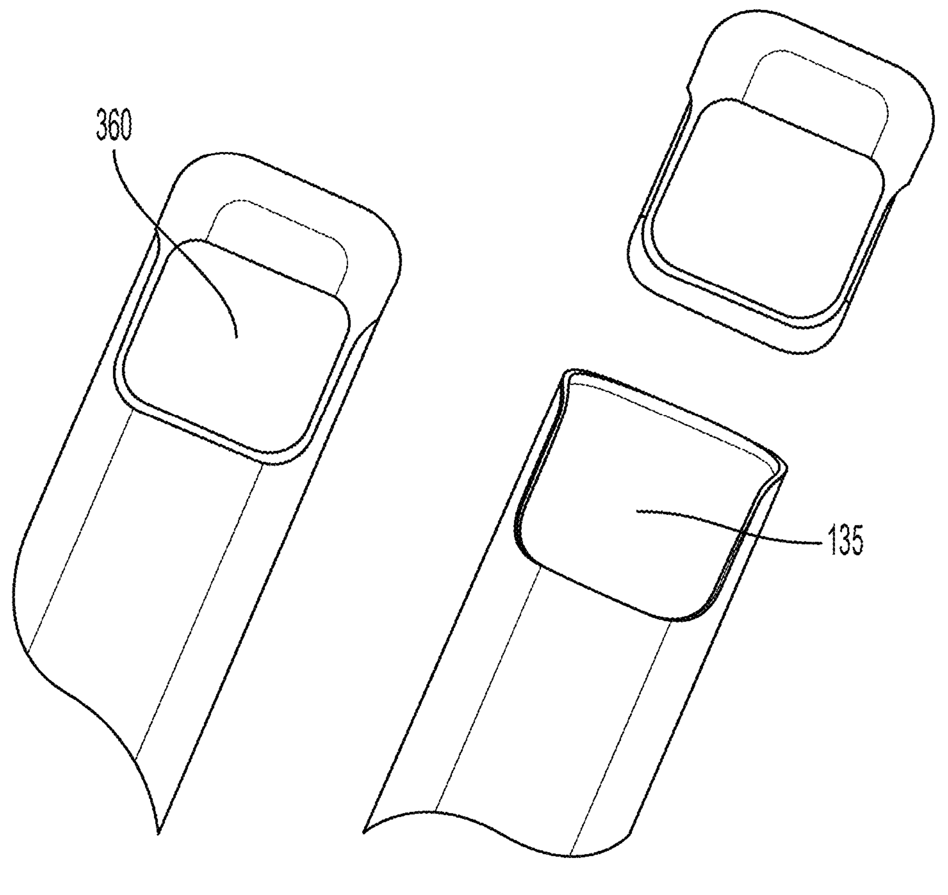
Figure 10:
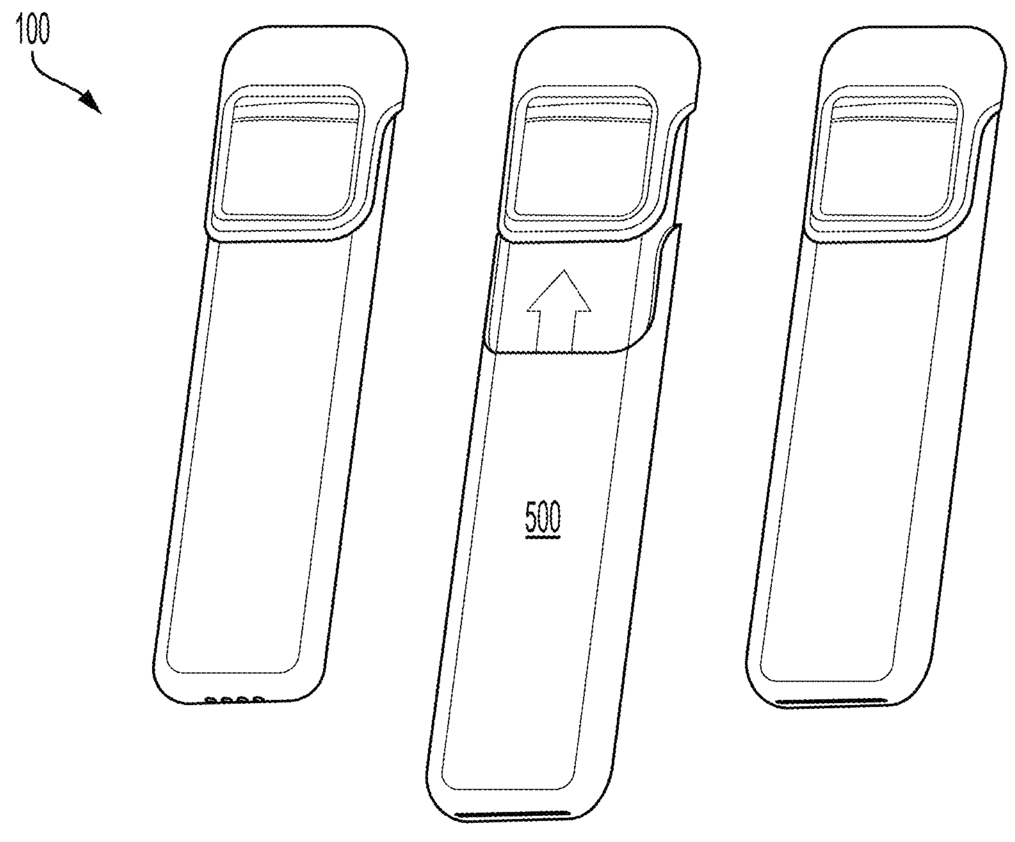

Having thus described the disclosure in the foregoing general terms, reference will now be made to the accompanying drawings, which are not necessarily drawn to scale, and wherein:

FIG. 1A illustrates a front perspective view of an aerosol delivery device, according to example implementations of the present disclosure;

FIG. 1B illustrates a back perspective view of an aerosol delivery device, according to example implementations of the present disclosure;

FIG. 2 illustrates a front partial cross-section of the device illustrated in FIG. 1A and FIG. 1B;

FIG. 3 illustrates a side partial cross-section of the device illustrated in FIG. 1A and FIG. 1B;

FIG. 4 is a perspective view of a cartridge according to example embodiments of the present disclosure;

FIG. 5A illustrates an exploded perspective view of a cartridge illustrating components useful in an aerosol delivery device, according to an example implementation of the present disclosure;

FIG. 5B illustrates a corresponding section view of the cartridge of FIG. 5A illustrating the components useful in an aerosol delivery device, according to an example implementation of the present disclosure;

FIG. 6A is a perspective view of a cartridge according to example embodiments of the present disclosure;

FIG. 6B is an exploded view of the cartridge illustrated in FIG. 6A;

FIG. 7A is a perspective view of a cartridge according to example embodiments of the present disclosure;

FIG. 7B is an exploded view of the cartridge illustrated in FIG. 7A;

FIG. 8A is a perspective view of a cartridge according to example embodiments of the present disclosure;

FIG. 8B is an exploded view of the cartridge illustrated in FIG. 8A;

FIG. 9 is a perspective view of an aerosol delivery device, according to example implementations of the present disclosure; and FIG. 10 is a perspective view of an aerosol delivery device and an associated sleeve, according to example implementations of the present disclosure.

DETAILED DESCRIPTION

Some implementations of the present disclosure will now be described more fully hereinafter with reference to the accompanying figures, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. Like reference numerals refer to like elements throughout.

As used in the specification, and in the appended claims, the singular forms "a", "an", "the", include plural referents unless the context clearly dictates otherwise. Unless specified otherwise or clear from context, references to first, second or the like should not be construed to imply a particular order. A feature described as being above another feature (unless specified otherwise or clear from context) may instead be below, and vice versa; and similarly, features described as being to the left of another feature else may instead be to the right, and vice versa. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As used herein, unless specified otherwise or clear from context, the "or" of a set of operands is the "inclusive or" and thereby true if and only if one or more of the operands is true, as opposed to the "exclusive or" which is false when all of the operands are true. Thus, for example, "[A] or [B]" is true if [A] is true, or if [B] is true, or if both [A] and [B] are true. Further, the articles "a" and "an" mean "one or more," unless specified otherwise or clear from context to be directed to a singular form. Furthermore, it should be understood that unless otherwise specified, the terms "data," "content," "digital content," "information," and similar terms may be at times used interchangeably.

Example implementations of the present disclosure are generally directed to delivery systems designed to deliver at least one substance to a user, such as to satisfy a particular "consumer moment." The substance may include constituents that impart a physiological effect on the user, a sensorial effect on the user, or both.

As described hereinafter, embodiments of the present disclosure relate to aerosol delivery devices or vaporization devices, said terms being used herein interchangeably. Aerosol delivery devices according to the present disclosure use electrical energy to heat a material (preferably without combusting the material to any significant degree and/or without significant chemical alteration of the material) to form an inhalable substance; and components of such devices have the form of articles that most preferably are sufficiently compact to be considered hand-held devices. That is, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery devices may be characterized as electronic cigarettes, and those electronic cigarettes most preferably incorporate tobacco and/or components derived from tobacco, and hence deliver tobacco derived components in aerosol form.

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosolizable composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

In various implementations, the present disclosure relates to aerosol delivery devices and cartridges and control devices that together comprise an aerosol delivery device. As will be described in more detail below, the aerosol delivery device of the present disclosure comprises a pod (also referred to herein as a "removable cartridge") which is insertable into a holster (also referred to herein as a "control body"). The pod and the holster are configured such that the pod can only be inserted into the holster one way.

An example implementation of an aerosol delivery device 100 of the present disclosure is shown in FIGS. 1A and 1B. FIG. 1A is a front perspective view of an aerosol delivery device 100, which includes a control device 200 and a removable cartridge 300. FIG. 1B is a back perspective view of an aerosol delivery device 100, which includes a control device 200 and a removable cartridge 300. Although only one cartridge is shown in the depicted implementation, it should be understood that, in various implementations, the aerosol delivery device 100 may comprise an interchangeable system. For example, in one or more implementations, a single control device may be usable with a plurality of different cartridges. Likewise, in one or more implementations, a single cartridge may be usable with a plurality of different control devices.

As seen in FIG. 1A, the control device 200 comprises a device outer housing 102 that defines a control device outer wall 104, a control device distal end 106, and a control device proximal end 108. As illustrated in FIG. 2, the control device proximal end 108 includes an opening 110 that provides access to a cartridge receiving chamber 112. The control device outer housing 102 comprises a front outer wall 113 and a back outer wall 114 which are connected to each other at side walls 115 and at a bottom outer wall 111 at the distal end 106 of the control device. In various embodiments, each of the front outer wall 113 and the back outer wall 114 can be substantially rectangular in shape. In various embodiments, one or more corners 117 of the front outer wall 113 and/or the back outer wall 114 can be rounded. The side walls 115 of the control device can also be substantially rectangular in shape. In various embodiments, the side walls 115 can be rounded such that the side walls are convex in shape.

As illustrated in FIG. 2, for example, the back outer wall 114 has a length L1. The front outer wall 113 has a length L2. In various embodiments L1 can be greater than L2. In certain embodiments, the side walls 115 can have a length that his substantially equal to the length of the back outer wall 114. As described in more detail below, this can allow for a front surface of the removable cartridge 300 to be exposed when connected to the control device 200. In certain embodiments, such a configuration can also ensure that the removable cartridge 300 can only be inserted into the control device 200 in a single orientation.

The nature of the control device is further evident in relation to FIG. 3, which shows a partial cross section of the control device 200. As seen therein, the control device 200 further includes a device battery 116 positioned within the device outer housing 102 and also includes a device external connection element 118. Preferably, the device external connection element 118 is positioned at the distal end 106 of the device outer housing 102. Control device electrical connector(s) 120 are positioned in the cartridge receiving chamber 112 and, as illustrated, protrude through an inner frame wall 119 such that the control device electrical connector(s) 120 can contact a bottom surface of a cartridge 300 when the cartridge is inserted into the control device 200. It is understood, though, that the device electrical connector(s) 120 may be positioned in any location within the cartridge receiving chamber 112. For example, the first device electrical connector(s) 120 may be positioned at a point on the sidewalls 115 between the proximal end 108 of the first device outer housing 102 and the inner frame wall 119. In some embodiments, the control device electrical connector(s) 120 (also referred to as "conductive pins) can comprise spring-loaded contacts which are configured to substantially align with corresponding features of a cartridge 300.

The various components of an aerosol delivery device according to the present disclosure can be chosen from components described in the art and commercially available. In the depicted implementation, the battery may comprise a lithium polymer (LiPo) battery; however various other batteries may be suitable. Some other examples of batteries that can be used according to the disclosure are described in U.S. Pat. App. Pub. No. 2010/0028766 to Peckerar et al., the disclosure of which is incorporated herein by reference in its entirety. In some implementations, other types of power sources may be utilized. For example, in various implementations a power source may comprise a replaceable battery or a rechargeable battery, solid-state battery, thin-film solid-state battery, rechargeable supercapacitor or the like, and thus may be combined with any type of recharging technology, including connection to a wall charger, connection to a car charger (e.g., cigarette lighter receptacle, USB port, etc.), connection to a computer, such as through a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

In various embodiments, the control device external connection element 118 may be configured for connecting to an external connector and/or a docking station or other power or data source. For example, in some implementations an external connector may comprise first and second connector ends that may be interconnected by a union, which may be, for example, a cord of variable length. In some implementations, the first connector end may be configured for electrical and, optionally, mechanical connection with the device (100,200), and the second connector end may be configured for connection to a computer or similar electronic device or for connection to a power source. An adaptor including a USB connector at one end and a power unit connector at an opposing end is disclosed in U.S. Pat. App. Pub. No. 2014/0261495 to Novak et al., which is incorporated herein by reference in its entirety. In various embodiments, a pin seal can be provided and configured to seal the interface between the external connection element 118 and the bottom surface 111 of the control device 200. In such a manner, the pin seal may be made of a silicone, thermoplastic polyurethane, or another resilient material. In the depicted implementation, one or more pins of the external connection element 118 may extend through the bottom surface 111 of the control device as noted above.

The aerosol delivery device 100 of the depicted implementation includes a control mechanism in the form of the control component 125, which is configured, in part, to control the amount of electric power provided to the heating member of the cartridge. Although other configurations are possible, the control component 125 of the depicted implementation comprises a circuit board 126 (e.g., a printed circuit board (PCB)) that includes both rigid and flexible portions. In particular, the circuit board 126 of the depicted implementation includes a rigid central section 126A and at least one rigid end section 126B which can either be a proximal end section (as illustrated in FIG. 3, for example) a distal end section (not pictured), with the at least one end section 126B being connected to the central section 126A by a respective flexible connection. In such a manner, when battery 116 and circuit board 126 are assembled into the control device 200, the central section 126A of the circuit board 126 is configured to be disposed proximate a major surface of the battery 116, and the at least one end section 126B is configured to be disposed substantially perpendicular to the central section 126A. In particular, the proximal end section 126B of the circuit board 126 is configured to extend over the top of battery 116. A distal end section is configured to extend over the bottom of the battery 116. The control device 200 is also configured to contain a vibration motor 130. The control device can further include motor housing, into which the vibration motor 130 is received. In various implementations, the vibration motor may provide haptic feedback relating to various operations of the device 100. The central section 126A of the depicted circuit board 126 also includes electrical contacts that are configured to operatively connect the circuit board 126 to the vibration motor 130.

In some embodiments, the control device outer wall 104 can also include an indicator in the form of a light source 140. In some implementations, the light source may comprise, for example, at least one light emitting diode (LED) capable of providing one or more colors of light. In other implementations, the light source may be configured to illuminate in only one color, while in other implementations, the light source may be configured to illuminate in variety of different colors. In still other implementations, the light source may be configured to provide white light. In the depicted implementation, the light source 140 comprises an RGB (red, green, blue) LED that is configured to provide a variety of colors of light, including white light. When assembled, the light source 140 can be positioned in or proximate to an aperture defined in the control device outer wall 104. In certain embodiments, the aperture comprises a narrow, elongate opening; however, in other implementations, the aperture may be provided in any desired shape and may be positioned at any location on the control device 200. In various implementations, further indicators (e.g., other haptic feedback components, an audio feedback component, or the like) can be included in addition to or as an alternative to the indicators included in the depicted implementation. Additional representative types of components that yield visual cues or indicators, such as LED components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties.

Other types of electronic components, structures and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference. Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

It is noted that the control device may include an inner frame that is a separate element from the control device outer housing 102. In other words, in certain embodiments, the chamber within the control device outer housing 102 is not merely an interior space that is defined by the outer housing. Rather, an inner frame defining the chamber exists independently and separately from the outer housing. The opening of the chamber may coincide with the opening at the proximal end of the outer housing. The inner frame, which includes inner frame wall 119, thus may a completely different element that is attached to the outer housing. Alternatively, the inner frame and the outer housing may be continuously formed. In either case, however, the sidewalls forming the inner frame are present interior to and separated from the outer housing. See, e.g., the devices described in U.S. patent application Ser. No. 16/598,496, filed Oct. 10, 2019, which is herein incorporated by reference in its entirety.

The device outer housing may be formed of any suitable material, such as a metal, plastic, ceramic, glass, or the like. Preferably, the control device inner frame (e.g., inner frame wall 119) is formed of the same material as used to form the control device outer housing 102; however, different materials may be used. Choice of materials as noted above may also extend to the device outer housing for any further control device(s) that are included in the vaporization system and/or to the cartridge outer housing.

As noted above, a portion of the cartridge 300 is configured to be coupled with the cartridge receiving chamber 112 of the control device 200 such that mechanical and electrical connections are created between the cartridge 300 and the control device 200. In particular, when the cartridge 300 of the depicted implementation is coupled with the control device 200, an electrical connection can be created between the electrical connector(s) 120 and corresponding features of the cartridge 300. As such, when the cartridge 300 is received in the receiving chamber 112 of the control device 200, the cartridge 300 may be operatively connected to one or both of the control component 125 and the battery 116 of the control device 200. Thus, when the cartridge 300 of the depicted implementation is coupled with the control device 200, the cartridge 300 is mechanically biased into connection with the control device 200 such that electrical connection is maintained between the cartridge and the control device. It should be understood that for the purposes of the present disclosure, the term "operatively connected" and other related forms thereof should be interpreted broadly so as to encompass components that are directly connected and/or connected via one or more additional components.

The presently disclosed system may comprise a single control device. Such single control device can be interchangeably connectable with a plurality of cartridges to form a plurality of different vaporization systems. For example, the control device may be interchangeably connectable with a first cartridge to form a first functioning vaporization system having a first set of characteristics, and the control device may be interchangeably connectable with a second cartridge to form a second functioning vaporization system having a second, different set of characteristics. Such vaporization can comprise two different cartridges, three different cartridges, or an even greater number of different cartridges that are all interchangeable with the first control device.

The presently disclosed system may comprise a plurality of control devices and/or a plurality of cartridges that can be interchangeably connectable to form a variety of functioning devices. In some embodiments, however, a cartridge can be specifically configured to be connectable to a control device in a single orientation, and a given control device can be specifically configured for connection with a given cartridge, and a given cartridge can be specifically configured for connection with a given control body.

As noted above, a portion of the cartridge 300 is configured to be coupled with the cartridge receiving chamber 112 of the control device 200 such that mechanical and electrical connections are created between the cartridge 300 and the control device 200. As can be seen in FIGS. 2-4, for example, the control device 200 and the cartridge 300 can be configured in such a way that the cartridge 300 is insertable into the control device 200 in only one orientation of the cartridge. As described above, the back outer wall 114 of the control device 200 can be longer than the front outer wall 113. As such, and as illustrated in FIG. 9 for example, when the cartridge 300 is inserted into the control device 200, the back side of the cartridge will be at least at least partially covered by the back outer wall 114 of the control device 200, particularly such that only the mouthpiece of the cartridge extends beyond the end of the back wall of the control device. In certain embodiments, at least a portion of side walls of the cartridge 300 will also be covered by the side walls 115 of the control device 200. The control device 200 can be configured in some embodiments so that at least a portion of the tank 310 is visible when the cartridge 300 is engaged with the control device, and the visible portion may particularly be limited to only a front surface of the cartridge.

A cartridge for use in an aerosol delivery device is provided herein. As illustrated in FIG. 4, for example, a cartridge 300 can comprise an outer housing 350 defining each of a tank 310 configured to contain an aerosolizable composition, an exit portal 315 at a proximal end 352 of the outer housing 350, and an aerosol path 375 (e.g., extending through at least a portion of the cartridge. The cartridge 300 can further comprise a bottom cap 326 defining a distal end 354 of the outer housing 305 that is configured for insertion into the receiving chamber 112 of a control device 200. The outer housing 350 defines a front face portion 360 and a rear face portion 365 interconnected with sidewalls 370 such that the outer housing 350 has a width W defined between the sidewalls and a thickness T defined between the front face portion and the rear face portion, the width W being greater than the thickness T.

In various embodiments, the front face portion and the rear face portion of the cartridge 300 are substantially asymmetrical such that the cartridge engages a control device in only a single orientation. For example, as illustrated in FIGS. 6A, 7A, and 8A, the cartridge can include a ledge 402 that protrudes outwardly from the cartridge body. The ledge 402 can encircle the entire body of the cartridge such that when the cartridge 300 is engaged with the control body 200, the ledge is flush against the top periphery of the control device 200. As illustrated in FIGS. 6A, 7A, and 8A, for example, the ledge can extend further down the front face portion of the cartridge than it extends down the rear force portion of the cartridge. In various embodiments, the ledge 402 can at least partially define the boundaries and/or shape of a viewing window. As illustrated in FIGS. 6A, 7A, and 8A, for example, the ledge can have a substantially U-shape on the front face portion of the cartridge, and a substantially linear shape on the rear face portion of the cartridge, with substantially linear shaped portions on the cartridge sidewalls connecting the rear and front portions of the ledge 402. As illustrated in FIG. 1B and FIG. 9, for example, the ledge 402 (which can be configured to engage flushly with the top periphery of the control body 200) can be configured such that that only the mouthpiece of the cartridge extends beyond the end of the back wall of the control device. It is further noted that the ledge 402 can define a bottom edge of the front side of cartridge housing (as described in more detail below). Furthermore, the front face portion of the ledge 402 can be configured to fit against or to slightly overlap/cover a front side of the bottom cap 326 when the housing and the bottom cap are engaged.

In various embodiments, the cartridge 300 is configured such that when the cartridge is engaged with a control device, at least a portion of the rear face portion of the outer housing 350 is covered by the back outer wall 114 of the control device 200 (see, e.g., FIGS. 1-2 and 9). In other words, the outer wall 104 of the control device 200 can be configured to include a cut out 135 (see, e.g., FIG. 9), such that when the cartridge 300 is engaged with the device 200, a larger portion of the front face of the cartridge is visible than the rear face of the cartridge. As illustrated in FIGS. 1-3 and 9, the cut-out 135 in the control device 200, which can be formed by a front device wall having a length that is less than the length of the back and optionally side device walls, is located near the proximal end of the control device 200 and is configured as a U-shape or a square shape in the depicted implementations. It should be understood that in other implementations, the cut-out has any other shape.

As described in more detail below, the cartridge 300 can be formed of a plurality of components that are interconnected. For example, in one or more embodiments, the mouthpiece 302 of the cartridge 300 can be configured for engagement with the central housing portion 384. In one or more embodiments, the central housing portion 384 of the cartridge 300 can be configured for engagement with the bottom cap 326. For example, FIGS. 6A, 7A, and 8A show example embodiments of a cartridge 300 according to the present disclosure and FIGS. 6B, 7B, and 8B are exploded views of the cartridges illustrated in FIGS. 6A, 7A, and 8A, respectively. It is noted that the cartridges disclosed herein are not limited to the example embodiments illustrated in FIGS. 6A, 6B, 7A, 7B, 8A, and 8B. The various components of the cartridges described herein can be permanently or removably interconnected.

As illustrated in FIGS. 6A and 6B, for example, the cartridge 300 can comprise a mouthpiece portion 302, a housing 384, and a bottom cap 326 configured to fit together (e.g., snap together to form a mechanical connection between the elements) to from the cartridge 300. The mouthpiece 302 and housing 384 can be configured to fit together to form the outer housing 350 of the cartridge 300. As illustrated in FIG. 6B, for example, the outer housing 350 of the cartridge, in particular, the housing 384, can be configured to be at least partially transparent or translucent so that a tank 310 contained therein is visible externally. In certain embodiments, the housing 384 can substantially define a front face portion and a rear face portion of the outer housing 350, which are interconnected with sidewalls. The housing 384 can include a viewing window 358. In certain embodiments, the viewing window 358 can protrude outwards from the housing 384 such that the front face portion and the rear face portion of the outer housing 350 are substantially asymmetrical. The housing 384 can be configured to engage the bottom cap 326. In addition, the mouthpiece 302 can include an extension 380, which is configured to frame the viewing window 358 of the housing 384. The extension 380 can define a cutout 382 through which at least a portion of the viewing window 358 is visible. It is noted that the extension 380 can at least partially form the ledge 402 which encircles the cartridge body. It is further noted that the ledge 402 defines a bottom edge of the front side of outer housing 350. In various embodiments, the mouthpiece 302 can be opaque. As illustrated in FIG. 6A, the cartridge 300 is asymmetrical and configured to engage a control device 200 in only a single orientation. In addition, no portion of the viewing window 358 is defined by any portion of the control device 200 when the cartridge 300 is engaged with the control device 200.

As illustrated in FIGS. 7A and 7B, for example, the cartridge 300 can comprise a housing 404, and a bottom cap 326 configured to fit together (e.g., snap together to form a mechanical connection between the elements) to from the cartridge 300. A mouthpiece portion 302 and a front face portion 360 can combine to form the housing 404. It is noted that the mouthpiece 302 can be at least partially opaque and the front face portion 360 can be at least partially transparent or translucent. The housing 404 can define a front face portion 360 and a rear face portion 365 interconnected with sidewalls 370. As illustrated in FIG. 7B, for example, the mouthpiece 302 can be configured to include the rear face portion 365 and sidewalls 370 of the housing 404. The front face portion 360 of the housing 404 can include a viewing window 358. In certain embodiments, the viewing window 358 can protrude outwards from the front face portion 360. The front face portion 360, can be configured to be at least partially transparent or translucent. In addition, the mouthpiece 302 can include an extension 380, which is configured to fit around viewing window 358. The extension 380 can define a cutout 382 through which at least a portion of the viewing window 358 is visible. It is noted that the extension 380 can at least partially form the ledge 402 which encircles the cartridge body. It is further noted that the ledge 402 defines a bottom edge of the front side of housing 404. As illustrated in FIG. 7A, the cartridge 300 is asymmetrical and configured to engage a control device 200 in only a single orientation. In addition, no portion of the viewing window 358 is defined by any portion of the control device 200 when the cartridge 300 is engaged with the control device 200.

As illustrated in FIGS. 8A and 8B, for example, the cartridge 300 can comprise an outer housing 406 which can include different treatments configured to define different segments of the cartridge (e.g., a mouthpiece portion 302 and a front face portion 360). The housing 406 is configured to engage a bottom cap 326 to from the cartridge 300. As illustrated in FIG. 8B, for example, the housing 406 defines a front face portion 360 and a rear face portion 365 interconnected with sidewalls 370. At least a portion of the front face portion 360 can have a first treatment applied at least partially thereto, which is different and distinguishable from a second treatment applied to the rear face portion 365 and/or sidewalls 370. For example, the rear face portion and/or the sidewalls can be treated to be darker, opaque, and/or less transparent/translucent than at least a portion of the front face portion 360. The front face portion 360 of the housing includes a viewing window 358 which is transparent or translucent. The viewing window 358 can be treated to be more transparent or translucent than the rest of the outer housing 406. Although the entire outer housing can be translucent or transparent, the viewing window is configured such that the viewing window is distinguishable from the rest of the outer housing 406 either in the fact that it is more transparent/translucent that the rest of the outer housing, or in the fact that it is frosted a different shade than the remaining outer housing portions. As such, the viewing window is distinct from the remaining portions of the outer housing of the cartridge. As illustrated in FIG. 8A, the cartridge 8A includes a ledge 402 extending around and protruding outwardly from the housing 406. The ledge 402 is substantially asymmetrical as the ledge extends further down the front of the housing 406 than it extends down the back of the housing 406. It is noted that the ledge 402 defines a bottom edge of the front face portion 360 of the housing 406.

FIG. 5A illustrates an exploded view of a cartridge and FIG. 5B illustrates a cross-sectional view of a cartridge to provide illustrations of possible internal components that can be present in a cartridge according to the present disclosure. Although other configurations are possible, the cartridge 300 of the depicted implementation generally can include a mouthpiece 302, a mouthpiece insert 304, an upper aerosol channel insert 306, an upper cartridge seal 308, a tank 310 comprising a tank wall 311, a lower cartridge seal 312, a base member 314, a liquid transport element (e.g., a wick) 316, a heating member 318, a pair of heater connectors 320A, 320B, a pair of O-ring seals 322A, 322B, a pair of metal inserts 324A, 324B, and a bottom cap 326. It is noted that internal cartridge components can be configured to be situated in any part of the cartridges described herein (e.g., the mouthpiece portion, the central housing portion, the bottom cap element, or anywhere within the outer housing of the cartridge).

As shown in the figures, the mouthpiece 302 of the depicted implementation defines a proximal end and a distal end, with the proximal end of the mouthpiece 302 defining an exit portal 315 therein. The mouthpiece 302 (and the mouthpiece insert 304) may be made of a molded polymer material, such as, for example, a molded plastic material (e.g., polypropylene, acrylonitrile butadiene styrene (ABS), polyethylene, polycarbonate, Polyamide (Nylon), high impact polystyrene, and combinations thereof), although other materials are possible. The mouthpiece 302 of the depicted implementations is configured to be secured to the central housing portion 384, and in certain embodiments, the bottom cap element 326 via snap features included on one or both of the mouthpiece 302 and central housing portion 384/bottom cap element 326; however, other attachment methods are possible (e.g., via adhesives, heat staking/welding, ultrasonic welding, etc.).

In some implementations, the mouthpiece insert may exhibit a color associated with a distinctive characteristic of the cartridge. For example, in some implementations a cartridge of the present disclosure may include an aerosolizable composition that includes a distinctive characteristic such as, for example, a particular flavorant (as discussed infra), or a specific strength of nicotine, although any characteristic of the cartridge may be considered a distinctive characteristic. For the purposes of the current description, the term "color" should be interpreted broadly, for example covering any color or any shade of the same color. It should also be noted that in some implementations, certain colors may be commonly associated with particular distinctive characteristics (e.g., the color green may be associated with a mint flavorant, and the color red may be associated with an apple flavorant); however, in other implementations, certain colors may be associated with particular distinctive characteristics according to an index or guide, which may be provided or made available to a user. Examples of distinctive characteristics are described in U.S. patent application Ser. No. 16/171,920, titled Aerosol Delivery Device with Flavor Indicator, which is incorporated herein by reference in its entirety.

The tank 310 of cartridges described herein defines a proximal end and a distal end, wherein the mouthpiece 302 is configured to engage the proximal end of the tank 310 and the bottom cap 326 is configured to engage the distal end of the tank 310. In some embodiments, the tank 310 also defines a reservoir cavity 328 that includes a closed proximal end and an open distal end. As such, the reservoir cavity 328 of the tank 310 is configured to contain an aerosolizable composition (e.g., an e-liquid, an aerosol precursor composition, a consumable gel, etc.) therein. The closed proximal end of the reservoir cavity 328 allows the cavity to create a reliable seal on the top side of the aerosolizable composition column. This may prevent the seepage/entry of air into the reservoir cavity from the top end when the cartridge is held upright. This may also prevent air from entering from the top of the aerosolizable composition column, which may create a vacuum and may reduce the potential of the aerosolizable composition to leak from the bottom of the tank through the aerosolizable transport element or other passages.

In various embodiments, at least a portion of the outer tank wall 311 can be configured to be at least partially transparent or translucent so that the aerosolizable composition 323 contained therein is visible externally. As described above, the cartridge 300 can be configured to include a viewing window 358 through which the outer tank wall 311 and optionally any aerosolizable composition 323 present in the tank 301 can be visible. In various embodiments, the cartridge is configured such that the outer tank wall 311 is only visible at one surface (e.g., front face portion) of the cartridge. In some embodiments, at least a portion of the tank wall may be colored. In some implementations, the color can be configured so that the aerosolizable composition within the tank is still visible, such by using a transparent or translucent outer tank wall. In other implementations, the tank wall can be configured so that the outer tank wall has substantially opaque color. The tank 310 may be made of a molded polymer material, such as, for example, a molded plastic material (e.g., a copolyester material, such as, for example, Tritan™ copolyester, acrylonitrile butadiene styrene (ABS), polyethylene, polycarbonate, Polyamide (Nylon), high impact polystyrene, polypropylene, and combinations thereof), although other materials, including glass, are possible.

For aerosol delivery systems that are characterized as electronic cigarettes, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

In the depicted implementation, the aerosolizable composition, sometime referred to as an aerosol precursor composition or a vapor precursor composition or "e-liquid", may be in a liquid form and may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The aerosolizable composition can be provided in a variety of forms. For example, the aerosol precursor composition (or components thereof) can be provided in liquid form so as to allow the composition to flow from one or more reservoirs to the heater element, such as via capillary action through a wick or other porous material, or by active or passive flow, which can include valve control. As such, the aerosol precursor composition may be provided in liquid form in one or more reservoirs (e.g., tank 310) positioned sufficiently away from the heater element to prevent premature aerosolization, but positioned sufficiently close to the heater element to facilitate transport of the aerosol precursor composition, in the desired amount, to the heater element for aerosolization. Alternatively, the aerosol precursor composition can be at least partially saturated into a substrate that can be in direct contact with the heater element such that, upon heating, the aerosol precursor composition is released from the substrate. Still further, the aerosol precursor composition can be in the form of a foam, gel, or solid. The physical state of the aerosol precursor composition can be the state of the material at ambient conditions (e.g., temperature and pressure). Such embodiments particularly can allow for precise aliquots of the aerosol precursor material to be provided in contact with a heater element so as to provide a defined number of puffs. At least a portion of the gel (or aerosol precursor in another form) can be coated directly on the heater element, for example. Thus, the heater element can be characterized as being operatively positioned within the smoking article to be substantially in contact with at least a portion of the aerosol precursor composition.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In the depicted implementation, the reservoir cavity 328 is configured to hold approximately 1.5 mL of aerosol precursor composition. In other embodiments, the reservoir cavity 328 is configured to hold about 1 ml or more, about 2 ml or more, about 5 ml or more, or about 10 ml or more of the aerosol precursor composition.

In some implementations, the aerosolizable composition may include one or more flavorants. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be understood that reference to a flavorant should not be limited to any single flavorant as described above, and may, in fact, represent a combination of one or more flavorants.

As illustrated in example FIGS. 5A and 5B, the bottom cap member 326 of the cartridges described herein can be configured to engage and cover the open distal end of the reservoir cavity 328 of the tank 310. The lower seal 312 of the depicted implementation is configured form a substantially air tight and liquid tight seal between a lower portion of the tank 310 and the bottom cap 326. For example, the lower seal 312 can be configured so as to facilitate a substantially air tight and liquid tight seal between the base member 326 and tank 310. In various implementations, the lower seal 312 may be made of silicone rubber, boron nitride (BN) rubber, natural rubber, thermoplastic polyurethane, or another resilient material. In the depicted implementation, the base member 326 may be made of a molded polymer material, such as, for example, a molded plastic material (e.g., acrylonitrile butadiene styrene (ABS), polyethylene, polycarbonate, Polyamide (Nylon), high impact polystyrene, polypropylene, and combinations thereof), although other materials are possible.

The cartridges described herein can be configured to provide liquid flow passages for the aerosolizable composition contained in the reservoir cavity 328 of the tank 310 in order to facilitate transfer of the liquid to the liquid transport element 316. As shown in the figures, the liquid transport element 316 can be disposed within the base member 326 and extends between the aerosolizable composition in the reservoir cavity 328 and the heating member 318. The liquid transport element 316 may have any shape or size according to the specific design of the cartridge, and may be formed of a variety of materials configured for transport of a liquid, such as by capillary action. For example, in some implementations the liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In other implementations, the liquid transport element may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference in their entireties.

As shown in the figures, a heating member 318 can be configured to be disposed within the base member 326, or within the outer housing 350 of the cartridges describe herein. In particular, the heating member 318 can include a heating element configured to concentrate heat in an area of the heating element configured to be in contact with the liquid transport element 316. In the depicted implementation, the liquid transport element 316 and the heating member 318 comprise a heating assembly 334, which, together with the base member 314 and the bottom cap 326, define a vaporization chamber 332.

It should be noted that some implementations need not include a heating assembly, but, rather, may include an atomization assembly configured to generate an aerosol in another manner. Some examples of atomization assemblies that generate aerosols in other ways can be found, for example, in U.S. application Ser. No. 16/544,326, filed on Aug. 19, 2019, and titled Detachable Atomization Assembly for Aerosol Delivery Device, which is incorporated herein by reference in its entirety.

In various embodiments, the heating member 318 may be made of a metal material, such as a stainless steel material, including, but not limited to, 316L, 316, 304, or 304L stainless steel. In other implementations, the heating member may be made of a different material, such as, for example, Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference in its entirety. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. Other heaters are described in U.S. Pat. App. Pub. No. 2016/0345633 to DePiano et al., which is incorporated herein by reference in its entirety.

Although in other implementations additional and/or differing contact features may be provided, the heating member 318 of the depicted implementation includes a pair of contact holes 331A, 331B that are configured to connect the heating member 318 to the heater connectors 320A, 320B of the cartridge 300. In depicted implementation, the heater connectors 320A, 320B are made of a conductive material and are plated with nickel and/or gold. Examples of conductive materials include, but are not limited to, copper, aluminum, platinum, gold, silver, iron, steel, brass, bronze, graphite, conductive ceramic materials, and/or any combination thereof. In the depicted implementation, the contact holes 331A, 331B are configured to have an inner diameter that is less than an outer diameter of the mating portions of the heater connectors 320A, 320B. In some implementations, the contact holes may include one or more features (e.g., one or more fingers or extensions) that create an effective inner diameter that is less than an outer diameter of the mating portion of the heater connectors 320A, 320B. In such a manner, the contact holes 331A, 331B of the heating member 318 may create an interference fit with the upper ends of the heater connectors 320A, 320B such that the heating member 318 may maintain electrical contact with the heater connectors 320A, 320B. In the depicted implementation, the lower end of the heater connectors 320A, 320B are sealed around respective circumferential surfaces thereof by the pair of O-rings 322A, 322B, which are configured to form a substantially air tight and liquid tight seal between the heater connectors 320A, 320B and the bottom cap 326. In such a manner, the O-rings 322A, 322B of the depicted implementation may be made of silicone rubber, boron nitride (BN) rubber, natural rubber, thermoplastic polyurethane, or another resilient material.

In various embodiments, the bottom cap 326 of the depicted implementation is configured to be secured to the distal end of the tank 310 via snap features included on one or both of the bottom cap 326 and tank 310; however, other attachment methods are possible (e.g., via adhesives, heat staking/welding, ultrasonic welding, etc.). In the depicted implementation, the bottom cap 326 of the cartridge 300 includes a cartridge air inlet channel 330, which is located in an approximate center of a bottom surface of the bottom cap 326. Although other configurations are possible, in the depicted implementation the cartridge air inlet channel 330 has a nozzle-like shape. In particular, the cartridge air inlet channel 330 of the depicted implementation includes a first portion (proximate the bottom surface of the bottom cap 326), which has a substantially cylindrical shape and a second portion, which has a substantially conical shape and leads to the vaporization chamber 332. In such a manner, the internal diameter of the cartridge air inlet channel 330 decreases before leading to the vaporization chamber 332. This configuration may help to keep the air inlet channel 330 relatively clear of liquid build-up leading into the vaporization chamber 332.

Although other configurations are possible, the cartridge 300 of the depicted implementation also includes metal contact pin(s) 320 that are positioned in the bottom cap 326 and are configured to be exposed through the bottom surface thereof. In some embodiments, the metal pin(s) may be configured for a press or snap fit connection with the bottom cap 326. In other implementations, the metal inserts may be a product of an insert molding process such that the bottom cap 326 and the metal inserts 320 form a unitary part. In certain embodiments, the metal inserts 320 comprise any material configured to be attracted by a magnet, such as various ferromagnetic materials, including, but not limited, to iron, nickel, cobalt, alloys such as steel, and/or any combination thereof.

As noted above, when the cartridge 300 is coupled with the cartridge receiving chamber 112 of the control device 200, mechanical and electrical connections are created between the cartridge 300 and the control device 200. In particular, when the cartridge 300 of the depicted implementation is coupled with the control device 200, a magnetic connection can be created between magnets located in the upper frame of the control device and the metal inserts 320 located in the bottom cap 326 of the cartridge 300. In addition, when the cartridge 300 is coupled with the control device 200, an electrical connection is created between the metal pin 120 of the control device 200 and the contact pin(s) 320 of the cartridge. As such, when the cartridge 300 is coupled with the control device 200, the cartridge 300 is mechanically biased into connection with the control device 200 such that electrical connection is maintained between the cartridge 300 (and, in particular the heating assembly 334) and the control device (and in particular, the control component 125 and the battery 116), thereby allowing for the control device to direct electrical current to the heating member 318. This may occur, for example, when a puff on the aerosol delivery device 100 is detected (or, in other implementations, via actuation by the user, such as, for example, via a pushbutton). When a user of the aerosol device 100 of the depicted implementation draws on the mouthpiece 302, inlet airflow is directed into the device 100 via a gap between the cartridge 300 (e.g., an outer wall of the cartridge 300) and the control device 200 (e.g., an inner wall of the control device 200 defining the receiving chamber 230 thereof). As a user draws on the device 100, the air that enters the gap between the cartridge 300 and the control device 200 travels.

As illustrated in FIG. 10, for example, the aerosol delivery devices 100 described herein can further include a sleeve 500 configured to slide over at least a portion of the aerosol delivery device 100. In certain embodiments, the sleeve 500 can be configured to substantially fit over the entire outer surface of the control device 200. The sleeve can be configured to protect the aerosol delivery device from damage (e.g., due to dropping, water damage, etc.). In certain embodiments, the sleeve can be waterproof such that the aerosol delivery device is at least water-resistant when covered by the sleeve. In various embodiments, the sleeve can be colored and/or textured. In some embodiments, the sleeve 500 can include a design, a pattern, and/or a logo or other product information on an exterior surface of the sleeve. The sleeve 500 can be interchangeable. As such, a user of the aerosol delivery device can change the sleeve 500 for aesthetic and/or utility purposes.

In one or more embodiments, the aerosol delivery device 100 can further include an external connector configured for electrical contact with the device external connection element (e.g., device external connection element 118). The external connector can include a first connector end and a second connector end interconnected by a union, which may be, for example, a cord of variable length. The first connector end can be configured for electrical and, optionally, mechanical connection with the device 100. In particular, the first connector end can include an inset wall that can be received within a well present at the distal end 106 of the device 100, 200. The external connector can include a plurality of electrical pins interior to the inset wall configured for making a charging and/or information transferring connection with the device external connection element 118. In some embodiments, the device 100 can include a mechanical connector adjacent the device external connection element 118. The mechanical connector can be a magnet or a metal (or like element) that is adapted for magnetic attraction to a magnet. The first connector end of the external connector then can likewise include a mechanical connection element that is positioned between the inset wall and the electrical pins. The mechanical connection element can be a magnet or a metal (or like element) that is adapted for magnetic attraction to a magnet. The second connector end of the external connector can be configured for connection to a computer or similar electronic device or for connection to a power source. For example, the second connector end can have a Universal Serial Bus (USB) connection or an AC adaptor; however, a different connection may also be provided and/or an adapter may likewise be included. For example, an adaptor including a USB connector at one end and a power unit connector at an opposing end is disclosed in U.S. Pat. Pub. No. 2014/0261495 to Novak et al., which is incorporated herein by reference.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A cartridge for use in an aerosol delivery device, the cartridge comprising:

an outer housing configured to contain at least an aerosolizable composition, the outer housing including an exit portal at a proximal end thereof for passage of an aerosol; and a bottom cap positioned at a distal end of the outer housing that is configured for insertion into a receiving chamber of a control device of the aerosol delivery device;

wherein the outer housing defines a front face portion and a rear face portion interconnected with sidewalls such that the outer housing has a width defined between the sidewalls and a thickness defined between the front face portion and the rear face portion, the width being greater than the thickness;

wherein the outer housing defines a ledge that encircles the front face portion, the rear face portion, and the sidewalls;

wherein the ledge extends further down the front face portion than the rear face portion, such that the front face portion has an asymmetrical configuration relative to the rear face portion;

wherein the asymmetrical configuration of the ledge defined by the outer housing is effective such that the cartridge engages the control device of the aerosol delivery device in only a single orientation; and wherein the ledge has a substantially U-shape on the front face portion and a substantially linear shape on the rear face portion.

2. The cartridge of claim 1, wherein the outer housing comprises a mouthpiece situated at the proximal end of the outer housing, and wherein the exit portal is defined through the mouthpiece.

3. The cartridge of claim 2, wherein the mouthpiece comprises the rear face portion and the sidewalls of the outer housing.

4. The cartridge of claim 3, wherein the outer housing further comprises a central housing portion including a viewing window.

5. The cartridge of claim 4, wherein no portion of the viewing window is defined by the control device.

6. The cartridge of claim 4, wherein the viewing window is transparent.

7. The cartridge of claim 1, wherein the outer housing comprises a viewing window.

8. The cartridge of claim 7, wherein the viewing window is transparent.

9. The cartridge of claim 7, wherein at least a portion of the aerosolizable composition is visible through the viewing window.

10. The cartridge of claim 1, wherein the bottom cap is configured to engage a distal end of the outer housing.

11. The cartridge of claim 1, further comprising a heating assembly configured to heat the aerosolizable composition to generate an aerosol.

12. The cartridge of claim 1, wherein an aerosol path is defined through the outer housing and the exit portal.

13. The cartridge of claim 1, wherein at least a portion of the rear face portion is covered by a back wall of the control device when the cartridge is engaged with the control device, such that a larger portion of the front face portion is visible than the rear face portion.

14. The cartridge of claim 1, wherein the ledge protrudes outwardly from the outer housing.

15. The cartridge of claim 14, wherein the outer housing is configured to engage the bottom cap.

16. The cartridge of claim 1, wherein the front face portion of the ledge at least partially defines the shape of a viewing window.

17. The cartridge of claim 16, wherein no portion of the viewing window is defined by the control device.

18. The cartridge of claim 1, wherein the front face portion of the ledge is configured to partially cover a front side portion of the bottom cap.

* * * * *